United States Patent [19]

Zee-Cheng et al.

[11] 4,014,885
[45] Mar. 29, 1977

[54] ANTI-LEUKEMIC OXYGENATED BENZO[C]PHENANTHRIDINE COMPOUNDS

[75] Inventors: Kwang Yuen Zee-Cheng; Chia-Chung Cheng, both of Kansas City, Mo.

[73] Assignee: The United States of America as represented by the Department of Health, Education and Welfare, Washington, D.C.

[22] Filed: Mar. 10, 1975

[21] Appl. No.: 557,183

Related U.S. Application Data

[62] Division of Ser. No. 446,896, Feb. 28, 1974, Pat. No. 3,912,740.

[52] U.S. Cl. .................... 260/289 A; 260/289 C; 260/289 AZ
[51] Int. Cl.² ............................... C07D 217/16
[58] Field of Search ..... 260/289 AZ, 289 A, 289 C

[56] References Cited

OTHER PUBLICATIONS

Bailey et al., *J. Chem. Soc.*, (1950) p. 2277.
Zee–Cheng et al., *J. Pharm. Sci.*, vol. 59, (1970) pp. 1630–1632.
Wall et al., 162nd ACS Meeting, (1971) MEDI-34.

*Primary Examiner*—Paul M. Coughlan, Jr.
*Attorney, Agent, or Firm*—John S. Roberts, Jr.; Norman J. Latker; Thomas G. Ferris

[57] ABSTRACT

5,6-Dihydro-6-alkoxynitidine compounds of the formula

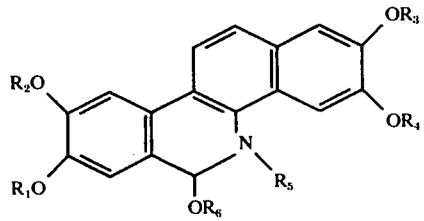

wherein $R_1$ and $R_2$ are selected independently from the group consisting of $C_1$-$C_6$ alkyl groups, H and benzyl or $R_1$ and $R_2$ taken together are methylene and $R_3$, $R_4$, $R_5$ and $R_6$ are selected independently from the group consisting of $C_1$-$C_6$ alkyl groups, H and benzyl are antileukemic agents.

3 Claims, No Drawings

ANTI-LEUKEMIC OXYGENATED BENZO[C]PHENANTHRIDINE COMPOUNDS

This is a division of application Ser. No. 446,896, filed Feb. 28, 1974, now U.S. Pat. No. 3,912,740.

This invention relates to a practical method for the synthesis of nitidine and related oxygenated benzo[c]-phenanthridine compounds. This invention further relates to the preparation of new compounds related to nitidine.

Nitidine chloride (I, $R_1$ and $R_2$ are methyl, $R_3$ and $R_4$ taken together are methylene, $R_5$ is methyl, $R_6$ is H—, and X is Cl) as well as 5,6-dihydro-6-methoxynitidine (II, $R_1$ and $R_2$ are methyl, $R_3$ and $R_4$ taken together are methylene, $R_5$ is methyl, and $R_6$ is methoxy) are oxygenated benzo[c]phenanthridine compounds as exemplified by formulas I and II.

Thus, there is a continuing need for a practical synthetic route giving reasonable yields of oxygenated benzo[c]phenanthridine compounds represented by formulas I and II.

It has been found, in accordance with this invention, that oxygenated benzo[c]phenanthridine compounds represented by formula I can be prepared in a practical fashion and further that hitherto unknown phenanthridine derivatives evaluated by standard procedures are active against L-1210 and P-388 mouse leukemia in mice and can be prepared by the method of this invention. Among the new compounds prepared in accordance with this invention are allonitidine compounds represented by the formula:

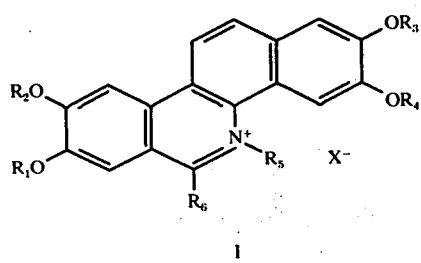

I

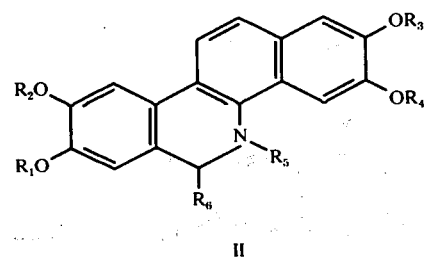

II highly cytotoxic and display anti-leukemic activity against mouse leukemia P-388 and L-1210 in mice. See, Wall et al., 162nd Meeting of the American Chemical Society, Washington, D.C. (1971), at MEDI-34.

Owing to the difficulty of obtaining the plants from which nitidine and related oxygenated benzo[c]-phenanthridine compounds were isolated and to the fact that both a somewhat related antileukemic alkaloid coralyne and the nitidine compound conform to a proposed N—O—O triangular pharmacophore hypothesis for antileukemic activity, as set forth by Zee-Cheng et al., J. Pharm. Sci., Volume 59 (1970), at 1630, it is apparent that a practical synthetic route to oxygenated benzo[c]phenanthridine compounds is needed.

The N—O—O pharmacophore hypothesis is based on the observation that several nonalkylating antileukemic agents have a common structural feature consisting of a triangulation composed of one nitrogen and two oxygen atoms with rather definite interatomic distances. It is proposed that this structural characteristic may contribute to the in vivo binding to one of the pertinent receptor sites involved in leukemia geneses.

Prior art on the synthesis of benzo[c]phenanthridine compounds include a Pschorr-type synthesis by ring closure of a diazotized aromatic amine to a fused ring structure reported by Dyke et al., Tetrahedron, Volume 24 (1968), at 1467, and the work of Arthur et al., J. Chem. Soc. (1961), at 4010. Neither of these reported routes is practical for the reason that the yields are unreasonably low.

Other available art on the synthesis of phenanthridine derivatives include Hellerbach, U.S. Pat. No. 3,243,438; Hellerbach et al., U.S. Pat. No. 3,499,901; and van der Burg, U.S. Pat. No. 3,661,916. However, none of these references provides a feasible route to

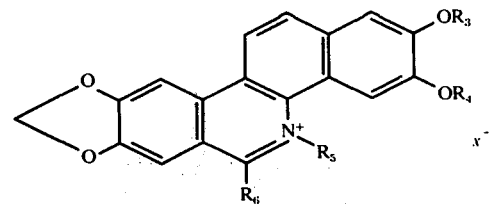

and 5,6-dihydro-6-alkoxynitidine compounds of the formula:

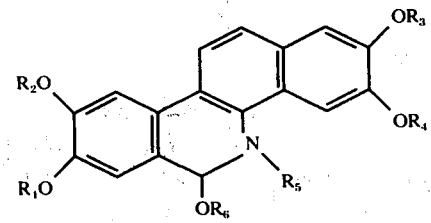

The method for synthesizing the oxygenated benzo[c]-phenanthridine compounds, represented by formula I, wherein $R_1$, $R_2$, $R_3$ and $R_4$ are selected independently from the group consisting of $C_1 - C_6$ alkyl, H, benzyl, $R_1$ and $R_2$ taken together are methylene and $R_3$ and $R_4$ taken together are methylene; $R_5$ is selected from the group consisting of $C_1 - C_6$ alkyl groups; $R_6$ is selected from the group consisting of H— and $C_1 - D_6$ alkoxy groups; and X is an anion, comprises the steps of:

condensing an oxygenated benzaldehyde derivative, represented by formula III, with an oxygenated benzophenone derivative, represented by formula IV,

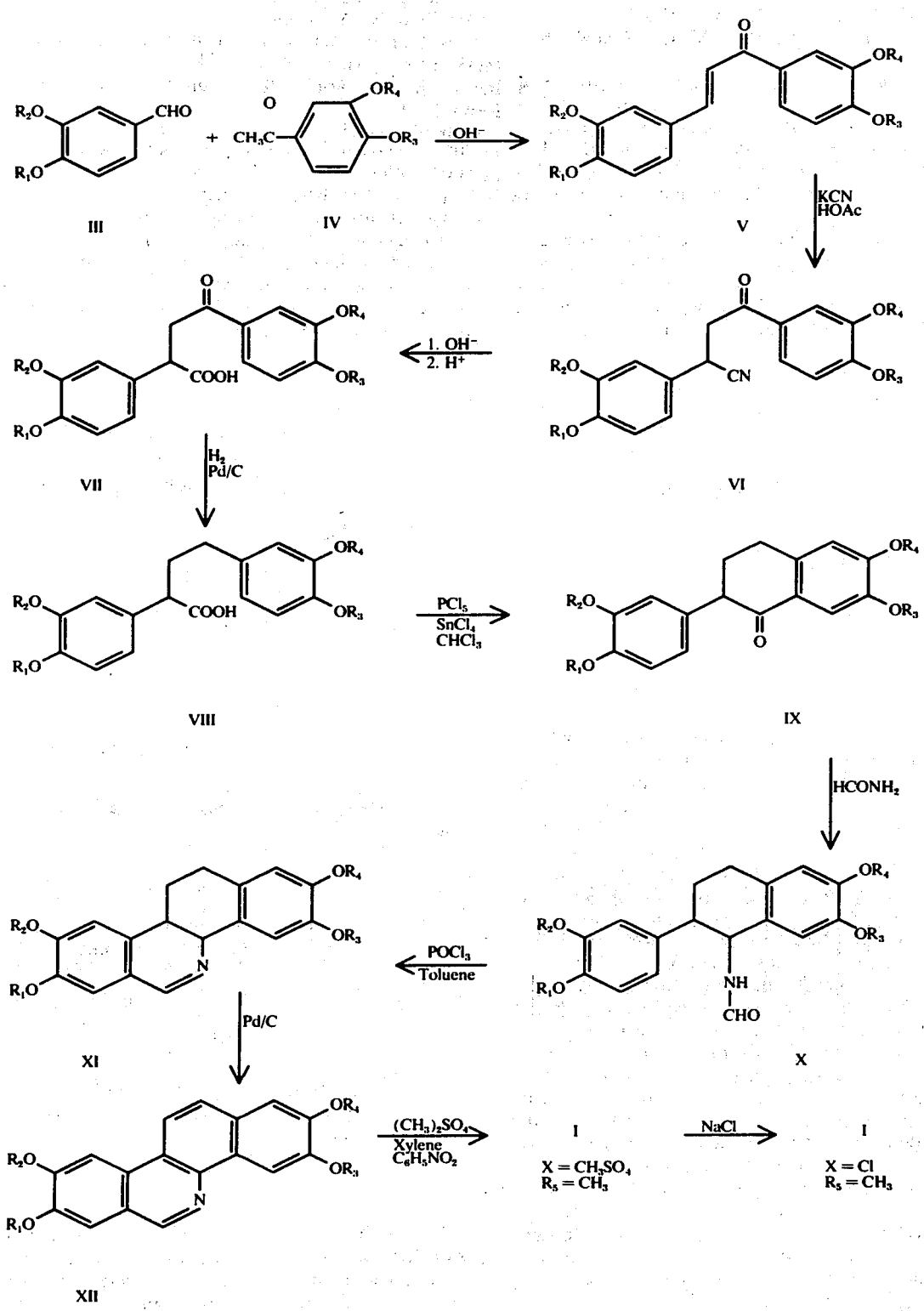

under alkaline conditions to form a chalcone, represented by formula V;

condensing the chalcone with a cyanide under acidic conditions to form a ketobutyronitrile, represented by formula VI;

hydrolyzing the ketobutyronitrile in a one-step base-catalyzed reaction to a ketobutyric acid, represented by formula VII;

reducing the ketobutyric acid to a butyric acid, represented by formula VIII;

cyclizing the butyric acid to a tetralone, represented by formula IX, using phosphorus pentachloride and stannic chloride as cyclizing agents;

converting the tetralone to a formamide represented by formula X, in a modified Leuckart reaction wherein the reaction mixture is heated at about 180°–185° C.,
cyclizing the formamide to a tetrahydrobenzo[c]-phenanthridine, represented by formula XI, with phosphorus oxychloride;
aromatizing the tetrahydrobenzo[c]phenanthridine over palladium on charcoal catalyst in an inert fluid of the phenyl polysiloxane type to a benzo[c]-phenanthridine, represented by formula XII;
and quaternizing the benzo[c]phenanthridine to I.

As to the foregoing synthetic sequence, it will be understood that the definitions of $R_1$, $R_2$, $R_3$, $R_4$, $R_5$, $R_6$ and X used in reference to the quaternized benzo[c]-phenanthridine, I, apply also to the substituents on compounds represented by formulas III–XII, as well as to the compounds represented by formula II for the dihydro derivatives.

It will further be understood that the term "oxygenated benzaldehyde derivative" includes compounds represented by formula III, "oxygenated benzophenone derivative" includes compounds represented by formula IV, "chalcone" includes compounds represented by formula V, and the like.

The synthetic route of this invention differs from the prior art and provides a practical synthesis of benzo[c]-phenanthridines because of four variations from previous syntheses, namely, (1) the one-step base-catalyzed hydrolysis of the ketobutyronitrile (VI) to the ketobutyric acid (VII) provides a better yield than hitherto available by a conventional two-step hydrolytic procedure via a ketoamide; (2) butyric acid (VIII) is cyclized to tetralone (IX) in higher yield than obtained by the conventional cyclization procedure using phosphorus oxychloride by low-temperature cyclization with phosphorus pentachloride and stannic chloride; (3) use of a higher than customary reaction temperature, that is, about 180°–185° C., in the Leuckart reaction between the tetralone (IX) and formamide increased the yield of the formamide derivative (X); and (4) the aromatizatiion of tetrahydrobenzo[c]phenanthridine (XI) to the phenanthridine (XII) using an inert fluid of the phenyl polysiloxane type, is much more selective than prior procedures, in which large amounts of undesired 11,12-dihydrobenzo[c]phenanthridine compounds are obtained.

In the case of nitidine methosulfate (I, $R_1$ and $R_2$ are methyl, $R_3$ and $R_4$ taken together are methylene, $R_5$ is methyl, $R_6$ is H—, and X is methosulfate), the overall yield from acetopiperone was 15%.

For the synthesis of allonitidine methosulfate (I, $R_1$ and $R_2$ taken together are methylene, $R_3$ and $R_4$ are methyl, $R_5$ is methyl, $R_6$ is H—, and X is methosulfate), the overall yield from dimethoxyacetophenone was 9%.

In the synthesis of compounds represented by formula I, it will be understood that the term "$C_1$ - $C_6$ alkyl, H, benxyl" as applied to $R_1$, $R_2$, $R_3$, $R_4$ and $R_5$, includes any of the normal or branched chain hydrocarbon radicals having from one to six carbon atoms, including methyl, ethyl, propyl, isopropyl, the butyl isomers, the amyl isomers, and the hexyl isomers. However, the preferred alkyl groups are the $C_1$- $C_4$ straight chain alkyl groups, that is, methyl, ethyl, propyl and butyl. Of these, methyl is particularly preferred.

It will further be understood that $R_6$ in formula I represents H— or an alkoxy group based on any $C_1$ - $C_6$ alkyl group, as previously defined. The preferred substituents represented by $R_6$ are H— and the $C_1$ - $C_4$ normal alkoxy groups, that is, methoxy, ethoxy, propoxy and butoxy. The most preferred are H— and methoxy.

The anion represented by X in formula I may be any monovalent negatively charged species which bonds ionically with nitrogen to form a quaternary salt. Typical of anions within the definition of X are chloride, bromide, iodide, hydroxide, methosulfate, and the monovalent equivalent of polyvalent anions such as sulfate, phosphate and the like. Of the foregoing anions, chloride, methosulfate and hydroxide are preferred in the practice of this invention. Methosulfate and chloride are particularly preferred.

As used in the specification and claims, "a cyanide" means sodium or potassium cyanide. The cyanide is condensed with the chalcone (VI) under acidic conditions to give a ketobutyronitrile (VI).

"One-step base-catalyzed reaction", as used in the specification and claims, means the reaction between the ketobutyronitrile derivative (VI) and an alkali, such as sodium hydroxide, potassium hydroxide or lithium hydroxide, in a medium of aqueous ethanol, to yield the ketoacid (VII).

Cyclization of butyric acid (VIII) to tetralone (IX), involving the use of a combination of phosphorus pentachloride and stannic chloride, is customarily done in an inert solvent, such as chloroform.

Conditions for the preparation of the formamide (X) from the tetralone (IX) include a temperature in the range from about 180° to about 185° C., although this is the temperature generally recommended for conversion of cyclic ketones to the corresponding primary amines, following a hydrolysis step omitted here. See Moore, in "Organic Reactions", Volume V (1949), after 301. In the synthesis of nitidine itself, a high temperature heating step is preferably followed by heating at a less elevated temperature, such as initially heating at about 180°–185° C. and then heating at about 140°–145° C.

The success of the aromatization of tetrahydrobenzo[c]-phenanthridines (XI) to benzophenanthridines (XII) depends on the use of a particular inert fluid, that is, a phenyl polysiloxane as exemplified by Dow Corning Fluids Nos. 550 and 710. The catalyst used in this procedure is a conventional palladium on charcoal catalyst. The reaction temperature is generally above 250° C., usually in the range from about 255° to about 260° C.

Normally, benzo[c] phenanthridines (XII) are quaternized with dimethyl sulfate to produce a methosulfate (I), which is converted by reaction with an ionic chloride, e.g., sodium chloride or potassium chloride, is a combination of solvents, e.g., xylene and nitromethane, to the chloride (I, X is Cl). The hydroxide (I, X is OH) is obtained from the halide in the usual manner, e.g., reaction in aqueous solution with silver hydroxide.

The benzo[c]phenanthridine methosulfate (I, $R_5$ is methyl, X is methosulfate) is also the intermediate from which 5,6-dihydrobenzo[c]phenanthridine (II) is obtained by reaction with aqueous ammonia. When the reaction between a benzo[c]phenanthridinium methosulfate and aqueous ammonia is followed by a reaction with methanol or any other alcohol, 5,6-dihydro-6-alkoxybenzo[c]phenanthridines are obtained (II, $R_5$ is methyl, $R_6$ is alkoxy).

The novel allonitidine compounds of this invention, as indicated by the formula above, are characterized by a methylenedioxy substituent at the 8 and 9 positions of the phenanthridine system and by alkyl groups $R_3$ and $R_4$ in the alkoxy groups at the 2 and 3 positions. The substituent at the 6-position, denoted by $R_6$, is selected from the group consisting of H— and $C_1$ - $C_6$ straight and branched chain alkoxy. $R_3$, $R_4$ and $R_5$ represent $C_1$ - $C_6$ alkyl, H. benzyl, whether or straight or branched chain structure. X is any of the anions listed above.

Preferably, $R_3$, $R_4$ and $R_5$ are methyl; $R_6$ is selected from the group consisting of H— and methoxy; and X is selected from the group consisting of chloride, hydroxide and methosulfate in the allonitidine compounds of this invention.

In the novel 5,6-dihydro-6-alkoxynitidine compounds of this invention, $R_1$, $R_2$, $R_3$, $R_4$, $R_5$ and $R_6$ are selected independently from $C_1$ - $C_6$ straight and branched chain alkyl groups and $R_1$ and $R_2$ taken together are methylene. The preferred novel dihydro compounds of this invention are those in which $R_1$, $R_2$, $R_3$, $R_4$, $R_5$ and $R_6$ are methyl and in which $R_1$ and $R_2$ taken together are methylene and $R_3$, $R_4$, $R_5$ and $R_6$ groups are methyl.

Reference is made to two articles by Zee-Cheng et al., *J. Heterocyclic Chem.*, Volume 10 (1973) at 85 and 867, wherein the synthesis of nitidine and related compounds and their biological activity is discussed, and which are hereby incorporated in this specification by reference.

Reference is also made to the standard testing procedures used in evaluating chemical agents, "Protocals for Screening Chemical Agents and Natural Products Against Animal Tumors and Other Biological Systems"(3rd Ed.), Cancer *Chemotherapy Reports*, Part 3, Volume 3, No. 2 (1972) at 7, for Lymphoid Leukemia L-1210, and at 9, for Lymphocytic Leukemia P-388.

The following examples illustrate the synthetic method of this invention and the preparation of novel compounds thereby.

EXAMPLE 1

3,4-Dimethoxy-3',4'-methylenedioxychalcone (V; $R_1$ and $R_2$ are methykl; $R_3$ and $R_4$ taken together are methylene).

3,4-Dimethoxybenzaldehyde (III; $R_1$ and $R_2$ are methyl) was condensed with acetopiperone (3,4-methylenedioxyacetophenone; IV; $R_3$ and $R_4$ taken together are methylene) according to Arthur et al., supra, except that an additional amount (30%) of 10% sodium hydroxide was used. The reaction mixture was warmed at 80°–90° C. for 10 minutes followed by overnight standing at room temperature. The yield was raised from 63% to 93%, melting point 133°–135° C., $\lambda$ max (ethanol) 254 (log 4.20), 360 nm (4.45).

EXAMPLE 2 α

-3,4-Dimethoxyphenyl)-γ-(3,4-methylenedioxyphenyl)-γ-oxobutyric acid (VII; $R_1$ and $R_2$ are methyl; $R_3$ and $R_4$ taken together are methylene).

A mixture of 76 grams (0.22 mole) of α-(3,4-dimethoxyphenyl)-γ-(3,4-methyledioxyphenyl)-γ-oxobutyronitrile (VI) prepared according to Arthur et al., supra, and 85 grams (2.13moles) of sodium hydroxide in 940 milliliters of water and 330 milliliters of ethanol was refluxed on a steam bath for 10 hours. It was then cooled and acidified with stirring, with 10% hydrochloric acid to pH 1. The resulting solid was collected by filtration, washed with water, and dried to give 77 grams (95% yield) of VII, melting point 168°–171° C. Recrystallization from ethanol, melting point 178°–179° C.; $\lambda$ max (ethanol) 230 (log $\epsilon$ 4.41), 274 (3.97) and 307 nm (3.92).

EXAMPLE 3

2-(3,4-Dimethoxyphenyl)-1,2,3,4-tetrahydro-6,7-methylenedioxy-1-oxanaphthalene (IX; $R_1$ and $R_2$ are methyl; $R_3$ and $R_4$ taken together are methylene).

A mixture of 20 grams (0.056 mole) of the product of Example 2 and 2.8 grams of 10% Pd/C in 200 milliliters of acetic acid in the presence of 1 milliliter of 70% perchloric acid was hydrogenated at 55°–60° C. under 4 kg./cm² for 2 hours. The resulting mixture was worked up as usual to yield 20 grams (95% yield) of the acid VIII as a light brown gummy residue; $\lambda$ max (ethanol) 234,283 nm.

To a stirred suspension of 12.0 grams (0.057 mole) of phosphorus pentachloride in 50 milliliters of dry chloroform was added a solution of 19.2 grams (0.056 mole) of VIII in 160 milliliters of chloroform with ice-bath cooling. The mixture was stirred in the ice bath for 2 hours followed by stirring at room temperature for 16 hours. To this was added dropwise, with ice cooling, a solution of 6.7 milliliters (0.056 mole) of anhydrous stannic chloride in 20 milliliters of chloroform in 30 minutes. The resulting mixture was stirred at ice bath temperature for 3 hours, then was poured into a mixture of 300 milliliters of 10% hydrochloric acid and 200 grams of ice. The gummy complex in the aqueous mixture was gradually dispersed and decomposed by stirring. The mixture was extracted with chloroform (4 × 400 milliliters). The resulting chloroform extracts were washed successivly with water, 3% sodium hydroxide, and water. The washings were back extracted with chloroform. The combined chloroform extracts were dried (sodium sulfate) and solvent removed in vacuo. The residue was triturated with 20 milliliters of methanol and the solid was collected by filtration to give 15.5 grams (84% yield) of IX, melting point 167°–170° C. Recrystallization from methanol yielded white needles, melting point 170°–172° C.; $\lambda$ max (ethanol), 232 (log $\epsilon$ 4.41), 275 (4.05) and 318 nm (3.97), m/e: 326 (M$^+$).

EXAMPLE 4

2-(3,4-Dimethoxyphenyl)-1-formamido-1,2,3,4-tetrahydro-6,7-methylenedioxynaphthalene, (X; $R_1$ and $R_2$ are methoxy; $R_3$ and $R_4$ taken together are methylene)

To a stirred mixture of 24 grams (0.074 mole) of the product of Example 3, 60 milliliters of redistilled formamide and 3.5 milliliters of formic acid was added 3.5 grams of ammonium sulfate. The reaction mixture was heated in an oil bath at 180°–182° C. for 6 hours with stirring. Cautious addition of one 3.5 milliliter portion of formic acid to the mixture was made each hour and there was a total of five such additiona. The resulting mixture was kept at 140°–145° C. for 12 hours. To the cooled mixture was added 100 milliliters of water and 150 milliliters of chloroform. After being stirred for 15 minutes, the aqueous layer was separated and extracted with chloroform (3 × 400 milliliters); the extract was combined with the organic layer, washed with water, dried (sodium sulfate), and solvent evaported. The resulting product was purified by column chromatography using neutral alumina and eluted with chloroform, Evaporation of the chloroform eluate yielded a residue, which, when triturated with 20 milliliters of methanol, gave 15.9 grams (55% yield) of X; melting point 168°–180° C. Recrystallization from methanol raised the melting point to 185°–187° C; ε max (ethanol): 230 (logλ 4.20), 285 nm (3.90), ε sh (ethanol) 293 nm (log ε 3.79), m/e: 355 (M+).

EXAMPLE 5

8,9Dimethoxy-2,3-methylenedioxy-4b,10b,11,12-tetrahydrobenzo[c]phenanthridine (XI; $R_1$ and $R_2$ are methyl; $R_3$ and $R_4$ taken together are methylene)

To a stirred suspension of 7.5 grams (0.021 mole) of the product of Example 4 in 75 milliliters of dry toluene at 115° C. was added 19 milliliters of redistilled phosphorus oxychloride. A yellow crystalline solid separated from the clear solution. The mixture was heated at that temperature for a total of 20 minutes and cooled to 40° C. The solid was collected by filtration, washed with toluene and ether, and dried to give 7.8 grams of the crude hydrochloride salt, melting point 211°–214° C. dec. This was suspended in 70 milliliters of warm methanol, basified with methanolic ammonia, and cooled. The resulting white crystals were collected by filtration, washed with methanol, and dried to give 4.7 grams (66% yield) of XI, melting point 188°–190° C. Recrystallization from methanol and pyridine yielded white crystals, melting point 198°–200° C. with decomposition; λ max (ethanol) 233 (log ε 4.52), 285 nm (4.07), m/e: 337 (M+).

EXAMPLE 6

8,9-Dimethoxy-2,3-methylenedioxybenzo[c]phenanthridine (2,3-dimethoxy-12-methyl[1,3-]benzodioxolo[5,6-c]phenanthridine, (XII; $R_1$ and $R_2$ are methyl; $R_3$ and $R_4$ taken together are methylene)

A mixture of 1 gram of the product of Example 5 and 0.3 gram of 30% palladium-on-charcoal catalyst prepared according to Mozingo, *Organic Synthesis*, Coll. Vol. III (1955), at 685, in 15 milliliters of Dow Corning 550 Fluid was heated under nitrogen at 255°–260° C. in an oil bath of 2 hours with stirring. The mixture was cooled and diluted with 50 milliliters of chloroform. The solid was removed by filtration and extracted continuously with chloroform. The combined filtrate and extracts were evaporated under reduced pressure to yield a pasty substance. This was triturated with 15 milliliters of ethanol. The resulting solid product was collected by filtration, washed with ethanol, and dried to give 0.85 gram (85% yield) of XII, melting point 276°–278° C. An analytical sample was obtained as white crystals by recrystallization from pyridine and ethanol, melting point 278°–280° C., λ max (ethanol) 229 (log ε 4.36), 274 (4.73), 311 (4.15), 348 (3.60), and 367 nm (3.46); λ sh (ethanol) 278 (4.71), 330 nm (3.89); thin layer chromatography Rf: 0.48 (chloroform, silica gel) Rf: 0.75 (chloroform, alumina); m/e: 333 (M+), 335 (M+ + 2H, trace). The product was found identical with that prepared by the previously reported "dry-heating" method, Arthur et al., supra.

Aromatization of the product of Example 5 to XII was also done by heating a mixture of XI and sulfur. The yield was comparable.

EXAMPLE 7

Attempted aromatization of XI.

Attempted aromatization of the product of Example 5 with palladium-on-charcoal in quinoline or with diphenyl disulfide yielded a solid, melting point 231°–233° C., which was identified as the 11,12-dihydronitidine derivative λ max (chloroform) 242 (log ε 4.28), 270 (4.52), 277 (4.60) and 326 nm (4.34).

Anal. Calcd. for $C_{20}H_{17}NO_4$ (335.4); C, 71.63; H, 5.11; N, 4.18. Found C, 71.30; H, 5.09; N, 4.31; m/e: 335·(M+, 100%).

EXAMPLE 8

Nitidine Methylsulfate (I; $R_1$ and $R_2$ are methyl; $R_3$ and $RR_4$ taken together are methylene; $R_5$ is methyl; $R_6$ is H—; X is $CH_3SO_4$)

To a solution of 2.2 grams (0.0066 mole) of the product of Example 6 in 25 milliliters of xylene and 50 milliliters of nitrobenzene at 160° C. was added 5 milliliters of dimethyl sulfate. This was heated at 180°–190° C. for 5 minutes whereupon a yellow solid separated from the reaction mixture. The mixture was cooled and diluted with 300 milliliters of ether. The solid was collected by filtration and washed with ether (3 × 100mmilliliters) to give 2.3 grams (73% yield) of nitidine methosulfate monohydrate, melting with decomposition at 307°–308° C. Recrystallization from methanol yielded an analytically pure sample, melting point 310°–312° C. (literature: Arther et al., supra, melts with decomposition at 306°–307° C.) The product was dried at 135° C. in vacuo before analysis; λ max (ethanol) 230 (log ε 4.38), 272 (4.68), 300 (4.54), 328 (4.50), and 388 nm (4.00), λ sh (ethanol) 280 nm (4.62). No moving spots were noted under either of the following thin-layer chromatography examinations: chloroform, silica gel or chloroform, alumina. Anal. Calcd. for $C_{22}H_{21}NO_8S \cdot H_2O$ (477.5): C, 55.34; H, 4.86; N, 2.93. Found: C, 55.63; H, 4.58; N, 2.98; m/e: 333 (M+-dimethylsulfate-water).

EXAMPLE 9

Nitidine Chloride (I; $R_1$ and $R_2$ are methyl; $R_3$ and $R_4$ taken together are methylene; $R_5$ is methyl; $R_6$ is H—; X is Cl).

In 100 milliliters of warm (70° C.) water was rapidly dissolved 250 milligrams 10.53 millimole) of the product of Example 8.

It was filtered immediately [the water-insoluble substance (48 milligrams], which separated from the aqueous solution, was identified as the unmethylated compound XII by comparison of their infrared spectra and this-layer chromatograms into 200 milliliters of stirred 15% sodium chloride solution. The light yellow solid, which separated from the saline solution by filtration, was dried and dissolved in 150 milliliters of boiling methanol. On cooling, a light, flocculent white solid separated from the solution. It was collected by filtration and dried to yield 30 milligrams of solid, melting point 303°–305° C. The solid was identified as the hydrochloride salt of XII by comparison of its infrared spectrum with that of an authentic sample.

Anal. Calcd. for $C_{20}H_{15}NO_4$ HCl (369.8): C, 64.96; H, 4.36; N, 3.79; Found: C, 65.20; H, 4.57; N, 3.79.

The filtrate was concentrated to 15 milliliters to give 60 milligrams (48% yield, based on starting material used) of nitidine chloride as light yellow crystals melting with decomposition at 275°–277° C. (Literature: Ishii et al., Yakagaku Zasshi, Val. 92 (1972), at 118, melting point 275°–276° C.); λmax (methanol): 234 (log ε4.39), 270 (4.67), 290 (4.62), 299 (4.61) 327 (4.60), and 380 nm (4.07).

The infrared spectrum of our synthetic compound was identical with that of the natural product provided by Drug Development Branch of the National Cancer Institute.

Anal. Calcd. for $C_{21}H_{18}ClNO_4 \cdot 2H_2O$ (4.19.8): C, 60.07; H, 5.28; N, 3.34. Found: C, 60.15; H, 5.24; N, 3.34; m/e; 333 ($M^+$-chloromethane-2water, 100%), 52 (48%), 50 (chloromethane, 100%).

EXAMPLE 10

5,6-Dihydro-6-methoxynitidine (II; $R_1$ and $R_2$ are methyl; $R_3$ and $R_4$ taken together are methylene; $R_5$ is methyl; $R_6$ is methoxy).

A mixture of finely ground nitidine methylsulfate hydrate (Example 8; 1 gram; 2.1 millimoles) in 140 milliliters of 28% aqueous ammonia was stirred in an ice bath for 20 minutes. The mixture was extracted with chloroform (3 × 300 milliliters). The extract was washed with water and dried (sodium sulfate). The solvent was removed under reduced pressure and the residue extracted with 100 milliliters of hot (50° C.) methanol (some insoluble solid was separated by filtration). The volume of the solution was reduced to 20 milliliters and 0.45 gram (56% yield) of II was collected as white crystals, melting point 186°–188° C. (dried at 78° C. in vacuo). Recrystallization from methanol yielded an analytically pure sample, melting point 189°–191° C. (softened at 186° C.); λmax (chloroform) 2.38 (log ε 4.53), 283 (4.60) and 310 nm (4.40); λ sh (chloroform) 325 nm (4.29). No moving spots were noted under the following thin-layer chromatography system; chloroform, silica gel. An Rf value of 0.2 was noted with chloroform, alumina. The product showed characteristics identical to those of the natural product. Prior to analysis, the sample was dried at 25° C. and 0.5 mm for 16 hours.

Anal. Calcd. for $C_{22}H_{21}NO_5$ (379.4): C, 69.64; H, 5.58; N, 3.69. Found: C, 70.00 H, 5.70; N, 3.73; m/e: 379 (12.9%, $M^+$), 348 (100%, $M^+$—$OCH_3$), 333 (17%, $M^+OCH_3$—$CH_3$).

EXAMPLE 11–18

Synthesis of Allonitidine (I; $R_1$ and $R_2$ taken together are methylene; $R_3$ and $R_4$ are methyl; $R_5$ is methyl; $R_6$ is H—; X is Cl).

EXAMPLE 11

3',4'-Dimethoxy-3,4-methylenedioxychalcone (V).

To a warm (40° C.) solution of 41.5 grams (0.23 mole) of 3,4-dimethoxyacetophenone and 40.5 grams (0.27 mole) of piperonal in 220 milliliters of ethanol was added 60 milliliters of 10 % aqueous sodium hydroxide. The mixture was warmed for 10 minutes at 40°–50° C; then stired at room temperature for 2 hours. After standing overnight, the yellow crystalline produce was collected by filtration, washed with water (3 × 40 milliliters), and dried to give 72 grams (quantitative yield) of V, melting point 127°–129° c. An analytical sample was prepared by recrystallization of 1.6 gram of the product from 50 milliliters of ethanol, giving 1.4 gram of pure chalcone as yellow needles, melting point 131°–133° C.; λmax (ethanol) 242 (log ε4.23), 3.60 nm (4.53).

Anal. Calcd. for $C_{18}H_{16}O_5$ (312.3): C, 69,22; H, 5.16. Found: C, 68.97; H, 5.26.

EXAMPLE 12

γ-(3,4-Dimethoxyphenyl)-α-(3,4-methylenedioxyphenyl)-γ-oxobutyronitrile) (VI)

A solution of 15 grams (0.23 mole) of potassium cyanide in 60 milliliters of water was added in 3 minutes, with stirring, to a hot (heated on a steam bath) solution of 36 grams (0.12 mole) of the product of Example 11 in 200 milliliters of 2-ethoxyethanol containing 7.5 milliliters (0.12 mole) of acetic acid. The resulting mixture was heated on a steam bath for 10 minutes and stirred at room temperature for 1 hour. To the mixture was added, at 0° C., 200 milliliters of water. The resulting white solid was collected by filtration, washed with water (3 × 150 milliliters), and dried to give 36 grams (92% yield) of VI, melting point 159°–161° C. Recrystallization from ethanol afforded an analytical sample, melting point 161°–162° C., λmax (ethanol) 230 (log ε4.34), 278 nm (4.16) λsh (ethanol) 306 nm (3.980.

Anal. Calcd. for $C_{19}H_{17}NO_5$ (339.4): C, 67.25; H, 5.05; N, 4.13. Found: C, 67.02; H, 4.96; N, 4.03.

EXAMPLE 13

γ-(3,4-Dimethozxyphenyl)-α-(3,4-methylenedioxyphenyl)-γ-oxobutyric Acid) (VII)

A mixture of 20 grams (0.059) of the product of Example 12 and 22 grams (0.55 mole) of sodium hydroxide in 250 milliliters of water and 90 milliliters of ethanol was refluxed on a steam bath for 10 hours. It as cooled and acidified with 10% hydrochloric acid to pH 1. The resulting mixture as stirred for 2 hours than allowed to stand overnight. The solid was collected by filtration, washed with water and dried, to give 23 grams (quantitative yield) of VII, melting point 198°–200° C. Recrystallization from ethanol yielded an analytically pure sample as white crystals, melting point 201°–203° C.; λmax (ethanol) 229 (log λ4.35), 274 nm (4.27); λsh (ethanol) 294 nm (4.14).

Anal. Calcd for $C_{19}H_{18}O_7$ (358.4); C, 63.68; H, 5.06. Found; C, 63.79; H, 5.02.

EXAMPLE 14

6,7-Dimethoxy-2-(3,4-methylenedioxyphenyl)-1-oxo-1,2,3,4-tetrahydronaphthalene) (IX)

A mixture of 22 grams (0.062 mole) of the product of Example 13 and 3 grams of 10% Pd/C in 200 milliliters of acetic acid in the presence of 1.5 milliliters of 70% perchloric acid was hydrogenated at 55°–60° C. under 4 kg./cm² for 2 hours. The catalyst was filtered from the warm reaction mixture and washed with acetic acid (3 × 40 milliliters). The combined filtrate and washings were evaporated to dryness in vacuo. The residue was extracted with benzene (4 × 300 milliliters). The benzene extract was washed with water (3 × 150 milliliters) and dried (sodium sulfate). Evaporation of solvent gave 20 grams (95% yield) of the butyric acid; λmax (ethanol) 230,280 nm.

To a stirred suspension of 25.5 grams (0.12 mole) of phosphorus pentachloride in 100 milliliters of dry chloroform was added a solution of 40 grams (0.115 mole) of the butyric acid in 300 milliliters of chloroform at 0° C. The resulting mixture was stirred in an ice bath for 2 hours and then at room temperature for 16 hours. To this was added dropwise at 0° C. a solution of 15 milliliters (0.12 mole) of anhydrous stannic chloride in 40 milliliters of dry chloroform in 15 minutes. The mixture was stirred at 0° C. for 3 hours and poured into a mixture of 450 milliliters of 10% hydrochloric acid and 200 grams of ice. The complex, which gradually decomposed, was extracted with chloroform (5 × 300 milliliters). The chloroform solution was washed successively with water (3 × 350 milliliters), 3% sodium hydroxide (3 × 350 milliliters) and water (3 ×]350 milliliters). The washings were back-extracted with chloroform. The combined chloroform solution was dried (sodium sulfate) and treated with Celite. The solvent was removed in vacuo and the residue triturated with 40 milliliters of methanol. The resulting solid was collected by filtration, washed with cold methanol, and dried to give 29.4 grams (77% yield) of IX, melting point 168°–179° C. Recrystallization from ethanol yielded an analytical sample as white needles, melting point 173°–175° C; λmax (ethanol) 233 (log ϵ4.31), 277 (4.13), 313 nm (3.91), m/e: 326 (M$^+$).

Anal. Calcd. for $C_{19}H_{18}O_5$ (326.4): C, 69.93; H, 5.56 Found: C, 70.16; H, 5.50.

EXAMPLE 15

6,7-Dimethoxy-1-formamido-2-(3,4-methylenedioxyphenyl)-1,2,3,4-tetrahydronaphthalene (X)

A stirred mixture of 24 grams (0.074 mole) of the product of Example 14, 3.5 grams of ammonium sulfate, 60 milliliters of formamide and 3.5 milliliters of formic acid was heated in an oil bath at 185° C. for 6 hours. Addition of a 3.5 milliliter portion of formic acid to the reaction mixture was made three times at hourly intervals. The reaction mixture was cooled and to it was added 150 milliliters of water followed by 250 milliliters of chloroform. The mixture was stirred for 15 minutes and transferred into a separatory funnel. The chloroform layer was separated and the aqueous layer extracted three times with chloroform. The combined chloroform solution was washed with water and dried (sodium sulfate). The solvent was evaporated in vacuo and the residue triturated with 50 milliliters of methanol. After it had stood overnight, the resulting white solid was collected by filtration to give 20.8 grams of crude X, melting point 150°–190° C. The crude product was purified on a neutral alumina column using chloroform as the eluent. Evaporation of the chloroform solution followed by recrystallization of the residue from methanol gave a pure product, melting point 201°–203° C.; λmax (ethanol) 233 (log ϵ4.19), 285 nm (3.98), m/e: 355 (M$^+$).

Anal. Calcd. for $C_{20}H_{21}NO_5$ (355.4): C, 67.59; H, 5.96; N, 3.94. Found: C, 67.44; H, 5.68; N, 3.99.

EXAMPLE 16

2,3-Dimethoxy-8,9-methylenedioxy-4b,10b, 11,12-tetrahydrobenzo[c]phenanthridine (XI)

To a stirred suspension of 3 grams (0.0085 mole) of the product of Example 15 in 30 milliliters of toluene was added 7.5 milliliters of redistilled phosphorus oxychloride. The mixture was heated at 100°–110° C. for 30 minutes, during which time a brown solution formed followed by precipitation of a yellow solid. The reaction mixture was cooled to 45° C., the solid was collected by filtration, washed with hot toluene and ether, and dried to give 2.4 grams of the hydrochloride salt of XI, melting with decomposition at 234°–235° C. The salt was suspended in 30 milliliters of methanol, basified with methanolic ammonia, and chilled. The resulting white solid was collected by filtration, washed with methanol, and dried to give 1.2 grams (42% yield) of XI, melting point 208°–210° C. Recrystallization from methanol and pyridine yielded white crystals, melting point 210°–212° C.; λmax (ethanol) 232 (log ϵ4.61), 280 (4.02), 316 nm (3.72), m/e: 337 (M$^+$).

Anal. Calcd. for $C_{20}H_{19}NO_4$ (337.4): C, 71.20; H, 5.68; N, 4.15. Found: C, 71.16; H, 5.88; N, 4.15.

EXAMPLE 17

2,3-Dimethoxy-8,9-methylenedioxybenzo[c]phenanthridine (XII).

A mixture of 0.5 gram (0.0015 mole) of the product of Example 16, 0.2 gram of 30% palladium-on charcoal and 7 milliliters of Dow Corning 550 fluid was heated under nitrogen at 255°–260° C. for 2 hours with stirring. The mixture was cooled, diluted with 30 milliliters of chloroform, and filtered. The catalyst was extracted continuously with chloroform. The combined filtrate and extract was evaporated in vacuo to a syrup which, upon trituration with 10 milliliters of ethanol, yielded a light yellow solid. This was collected by filtration, washed with ethanol and petroleum ether (boiling point 35°–60°C and dried to give 0.4 gram (80% yield) of XII, melting point 275°–277° C. (recrystallized from pyridinemethanol); λmax (chloroform) 273 (logϵ4.83), 283 (4.08), 305 (4.38), 333 (3.98), 351 (3.76), 368 nm (3.48); m/e: 333 (M$^+$).

Anal. Calcd. for $C_{20}H_{15}NO_4$ (333.4): C, 72.06; H, 4.54; N, 4.20. Found: C, 72.22; H, 4.79; N, 4.42.

EXAMPLE 18

Allonitidine Methyl Sulfate (2,3-Dimethoxy-8,9-methylenedioxy-5-methylbenzo[c]phenanthridinium Methyl Sulfate, of 2,3-Dimethoxy-5-methylbenzo[c][1,3]dioxolo[4,5-J]phenanthridinium Methyl Sulfate)(I).

To a hot solution of 11 grams (0.33 mole) of the product of Example 17 in 110 milliliters of xylene and 250 milliliters of nitrobenzene was added 30 milliliters of dimethyl sulfate. The mixture was heated at 175°–180° C. for 20 minutes with stirring whereupon a yellow solid gradually separated from the reaction mixture. The mixture was cooled and diluted with 250 milliliters of ether. The yellow solid was collected by filtration on a fritted glass funnel, washed with ether and petroleum ether (boiling point 35°–60° C.) and dried to give 13.9 grams (91% yield) of product, melting with decomposition at 322°–324° C. An analytical sample prepared by recrystallization from methanol, melted with decomposition at 328°–330° C. λmax (methanol), 231 (log ϵ4.43), 272 (4.80), 302 (4.59), 328 (4.51) and 390 (3.98); m/e: 333 (M$^+$-(CH$_3$)$_2$SO$_4$).

Anal. Calcd. for $C_{22}H_{21}NO_8S$ (459.5): C, 57.51; H, 4.61; N, 3.05. Found: C, 57.71; H, 4.41; N, 2.94.

EXAMPLE 19

5,6-Dihydro-6-methoxyallonitidine (5,6-Dihydro-5-methyl-8,9-methylenediozy-2,3,6-trimethoxybenzo[c]phenanthridine or 5,6 -Dihydro-5-methyl-2,3,6-trimethoxybenzo[c][1,3]dioxolo[4,5-j]-phenanthridine) (II); R$_1$ and R$_2$ taken together are methylene; R$_3$, R$_4$ and R$_5$ are methyl; R$_6$ is methoxy).

A mixture of 1.4 grams (3 millimoles) of finely ground allonitidine methyl sulfate and 200 milliliters of 28% aqueous ammonia was stirred in an ice bath for 30 minutes. The mixture was extracted with chloroform (5 × 200 milliliters), the extract washed with water (50 milliliters) and dried (sodium sulfate). To the dried solution was added 50 milliliters of methanol. The resulting mixture was evaporated below 30° C. in vacuo. The pasty residue was extracted with 150 milliliters of hot methanol. The methanol extract was concentrated to 50 milliliters and cooled. White crystals, which gradually separated from the solution, were collected by filtration, washed with ether and petroleum ether (boiling point 35°–60° C.), and dried to give 0.6 gram (54% yield) of II, melting with decomposition at 211°–213° C.; λmax (chloroform) 281 (log ϵ4.63), 311 nm (4.38); m/e: 379 (M⁺), 348 (M⁺-OCH₃), 333 (M⁺—OCH₃—CH₃).

Anal. Calcd. for $C_{22}H_{21}NO_5$ (379.4): C, 69,.64; H, 5.58; N, 3.69. Found; C, 69.40; H, 5.49; N, 3.62.

EXAMPLE 20

2,3,8,9-Tetramethoxy-5-methylbenxo[c]phenanthridinium Methyl Sulfate (I; $R_1$, $R_2$, $R_3$, $R_4$ and $R_5$ are methyl; $R_6$ is H—; X is $CH_3SO_4$).

Material prepared by the method of Examples 11–18 gave a tetramethoxy compound melting at 311°–312° C. The reported melting point is 305°–308° C.; Bailey et al., *J. Chem. Soc.* (1950), at 2277.

EXAMPLE 21

5,6-Dihydro-5-methyl-2,3,6,8,9-pentamethoxybenzo[c]phenanthridine (II; $R_1$, $R_2$, $R_3$, $R_4$ and $R_5$ are methoxy)

The product of Example 20 was converted, in 63% yield, to II according to the method of Example 19. The product melted at 212°–214° C., λmax (chloroform) 281 (log ϵ4.62 ) 310 nm (4.36); m/e: 395 (M⁺), 364 (M⁺—OCH₃), 349 (M⁺—OCH₃-CH₃).

Anal. Calcd. for $C_{23}H_{25}NO_5$ (395.5): C, 69.86; H, 6.37; N, 3.54. Found: C, 70.08; H, 6.14; N, 3.58.

What is claimed is:

1. 5,6-Dihydro-6-alkoxynitidine compounds of the formula

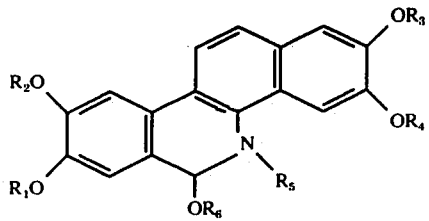

wherein $R_1$ and $R_2$ are selected independently from the group consisting of $C_1$-$C_6$ alkyl roups, H and benzyl or $R_1$ and $R_2$ taken together are methylene and $R_3$, $R_4$, $R_5$ and $R_6$ are selected independently from the group consisting of $C_1$-$C_6$ alkyl groups, H and benzyl.

2. The 5,6-dihydro-6-alkoxynitidine compound of claim 1, wherein $R_1$, $R_2$, $R_3$, $R_4$, $R_5$ and $R_6$ are methyl.

3. The 5,6-dihydro-6-alkoxynitidine compound of claim 1, wherein $R_1$ and $R_2$ taken together are methylene and $R_3$, $R_4$, $R_5$ and $R_6$ are methyl.

* * * * *

UNITED STATES PATENT OFFICE
CERTIFICATE OF CORRECTION

PATENT NO. : 4,014,885
DATED : March 29, 1977
INVENTOR(S) : Kwang Yuen Zee-Cheng and Chia-Chung Cheng It is certified that error appears in the above-identified patent and that said Letters Patent are hereby corrected as shown below:

Column 2, line 63, "$C_1-D_6$" should be -- $C_1-C_6$ --.

Column 6, line 15, "chalcone (VI)" should be --chalcone (V)--

Column 7, line 52, "(log   4.20)" should be --(log $\epsilon$4.20)--

Column 7, line 54, " -3,4-Dimethoxyphenyl)" should be -- $\alpha$-3,4-Dimethoxyphenyl) --

Column 8, line 58, "150 milliliters" should be --250 milliliters--

Column 9, line 1, " $\epsilon$max (ethanol)" should be -- $\lambda$ max (ethanol)--

Column 9, line 2, "(log $\lambda$4.20)" should be --(log $\epsilon$4.20)--

Column 9, line 2, " $\epsilon$sh" should be -- $\lambda$ sh--

Column 12, line 31, "(log $\lambda$ 4.35)" should be --(log $\epsilon$ 4.35)--

Column 12, line 13, "(3.980" should be --(3.98)--

Column 13, line 7, "179°" should be --170°--

Column 15, line 1, "54%" should be --52%--

Column 15, line 24, "methoxy)" should be deleted and the following inserted --methyl; $R_6$ is methoxy).--

Signed and Sealed this

Twenty-first Day of June 1977

[SEAL]

Attest:

RUTH C. MASON
*Attesting Officer*

C. MARSHALL DANN
*Commissioner of Patents and Trademarks*